United States Patent [19]
Blackman et al.

[11] Patent Number: 4,883,660
[45] Date of Patent: Nov. 28, 1989

[54] GEL BASES FOR PHARMACEUTICAL COMPOSITIONS

[75] Inventors: Steven T. Blackman, New York; Irene Ralske, North Bellmore, both of N.Y.

[73] Assignee: Thames Pharmacal Co., Inc., Ronkonkoma, N.Y.

[21] Appl. No.: 258,581

[22] Filed: Oct. 17, 1988

[51] Int. Cl.$^4$ .................. A61K 31/74; A61K 9/66; A61K 9/48

[52] U.S. Cl. ........................ 424/78; 424/456; 424/434; 424/464; 514/944; 514/941

[58] Field of Search ............. 424/78, 455, 456, 473, 424/435; 514/723, 944, 941

[56] References Cited

U.S. PATENT DOCUMENTS

| | | | |
|---|---|---|---|
| 4,276,430 | 6/1981 | Reller et al. | 560/252 |
| 4,759,924 | 7/1988 | Luebbe et al. | 424/42 |
| 4,775,678 | 10/1988 | Su et al. | 514/396 |

*Primary Examiner*—Joseph L. Schofer
*Assistant Examiner*—Carmen Pili-Curtis
*Attorney, Agent, or Firm*—Kirschstein, Ottinger, Israel & Schiffmiller

[57] ABSTRACT

Gel bases for pharmaceutical compositions comprise from about 0.5 to about 10.0% by weight ethoxylated (2 to 30 moles of ethoxylation) behenyl alcohol and from about 90 to 99.5% of a glycol solvent or from about 2.5 to about 10.0% by weight ethoxylated fatty alcohols having a chain length of from 16 to 21 carbon atoms and from 90 to about 97.5% of a glycol solvent. Preferred glycol solvents include propylene glycol and polyethylent glycols having an average molecular weight of about 200 to 800. Pharmaceutical compositions suitable for topical, transmucosal and oral administration may be prepared utilizing the novel gel bases. Methods of administration of topically, systemically and orally active pharmaceutical agents utilizing the novel gel bases are also provided.

10 Claims, No Drawings

GEL BASES FOR PHARMACEUTICAL COMPOSITIONS

BACKGROUND OF THE INVENTION

1. Field of the Invention

The invention relates to gel bases or vehicles for pharmaceutical compositions, compositions incorporating such bases and methods of administering medications utilizing such bases.

2. Description of the Prior Art

Pharmaceutical agents effective in topical application, e.g. for treating dermatological conditions, generally must be incorporated into a suitable ointment, lotion or cream vehicle to promote uniform application and effective transdermal absorption.

Originally, most vehicles for topical medicaments were in the nature of greasy ointments which are not water washable and have a tendency to adhere to and stain clothing. Moreover, the greasy composition of many ointments actually inhibits the release and absorption of many topically active pharmaceutical agents.

As an alternative to ointments, water-based creams were developed which are water washable and non-staining, and yet provide satisfactory spreadability and adherence while not inhibiting the release of active ingredients admixed therewith. These aqueous creams, however, are not suitable for use with active ingredients which are water-decomposable or water-insoluble. Furthermore, many of the aqueous creams of the prior art provide little or no occlusive coating to the treated area. In the case of certain topically active agents, such as anti-inflammatory steroids, therapeutic efficacy is substantially increased when the topical vehicle provides occlusion as well was adherence.

In order to combine the desirable unctuousness and pharmaceutical compatibility of oil-based ointments with the water miscibility and lightness of aqueous creams, anhydrous water washable bases have been developed which do not adversely affect moisture-degradable or water-insoluble ingredients, enable rapid release of the active agent and provide an occlusive coating for enhanced pharmaceutical activity. Such anhydrous creams are disclosed, for example, in U.S. Pat. Nos. 3,592,930 and 3,888,995. The specific cream vehicles described in the aforementioned patents consist primarily of propylene glycol and a saturated fatty alcohol having from 16 to 24 carbon atoms. Various plasticizers, coupling agents and penetrants are also taught as valuable additional ingredients.

While anhydrous creams disclosed in the prior art, e.g., the fatty alcohol/propylene glycol creams, are effective and have been commercially used for topical steroid preparations, they suffer from a number of drawbacks. These creams incorporate fatty alcohols having 16 or more carbon atoms, but commercially available $C_{16}$ to $C_{24}$ fatty alcohols contain as impurities significant amounts of unsaturated alcohols and alcohols having fewer than 16 carbon atoms. These short-chain alcohols are known irritants which may exacerbate rather than ameliorate the condition to be treated. Moreover, while propylene glycol is used in many topically active pharmaceuticals, particularly steroids (the higher the propylene glycol concentration, the less need there is for preservatives and the better the percutaneous absorption), the propylene glycol concentration in the known anhydrous creams cannot normally be increased beyond about 70% without decreasing the viscosity of the cream to the point where it resembles a lotion.

Alcohol-containing gels and gel-like vehicles for pharmaceutical agents are also known in the prior art. By way of example, U.S. Pat. No. 4,540,572 discloses a gel-like ointment containing indomethacin as well as ethyl alcohol to be applied topically, but intended to achieve systemic blood levels of the indomethacin for treatment of rheumatic diseases. Similarly, in U.S. Pat. No. 4,593,048, compositions incorporating high concentrations of lower alcohols, including such compositions in gel form, are disclosed. These prior art alcohol-containing gels, however, include extrinsic gelling agents, e.g. carboxymethyl cellulose, in addition to the alcohols and other ingredients of the pharmaceutical vehicle. Moreover, the alcohols utilized are short-chain alcohols (generally ethyl alcohol) which can be irritating, drying, and sensitizing, particularly when applied to broken or inflamed tissue areas.

Moreover, the alcohol-containing gels disclosed in the prior art would not be appropriate for transmucosal administration, for example, intranasally, buccally, or sublingually, because of the irritation and discomfort which would be caused thereby, and because of the possible detrimental effects of repeated application to the mucosa.

Gel-like formulations designed for systemic administration of pharmaceutical agents via transmucosal routes, particularly by the intranasal route, are disclosed in U.S. Pat. Nos. 4,383,993 and 4,394,390, among others. These gels, however, while innocuous and suitable for application to mucous membranes, are aqueous and therefore not usable with active ingredients that rapidly decompose or are insoluble in an aqueous vehicle and also require extrinsic gelling agents, which significantly add to the expense and time of manufacture and foster bacterial growth.

SUMMARY OF THE INVENTION

1. Objects of the Invention

It is an object of the present invention to provide anhydrous gel bases for incorporation into pharmaceutical compositions which overcome the aforementioned drawbacks in prior art topically applied vehicles for pharmaceutical agents.

Another object of the present invention is to provide bases as described above which can be produced using only glycol solvents and small quantities of surfactants, without the addition of any extrinsic gelling agents.

An additional object of the present invention is to provide bases as described above which maximize glycol content while maintaining a gel-like consistency.

Still another object of the present invention is to provide vehicles as described above which are suitable for topical application to the skin and mucosa, and which provide rapid penetration of any compatible pharmaceutical agent dissolved or suspended therein.

Yet a further object of the present invention is to provide bases as described above which can be incorporated into oral pharmaceutical dosage forms.

Still another object of the present invention is to provide pharmaceutical compositions which can be topically applied for topical and systemic therapies, and/or orally ingested, incorporating the gel bases as described above.

Yet an additional object of the present invention is to provide methods of administration of topical and systemic pharmaceutical agents utilizing the gel bases as described above.

2. Brief Description of the Invention

In keeping with these objects and others that will become apparent hereinafter, the present invention resides, briefly stated, in gel bases for pharmaceutical compositions comprising (a) from about 0.5 to about 10% by weight ethoxylated (2 to 30 moles of ethoxylation) behenyl alcohol and from about 90 to about 99.5% of a glycol solvent; or (b) from about 2.5 to about 10% by weight ethoxylated fatty alcohols having a chain length (prior to ethoxylation) of from 16 to 21 carbon atoms, and from about 90 to about 97.5% of a glycol solvent by weight. The invention also comprehends pharmaceutical compositions incorporating active pharmaceutical agents in the gel bases and optional additional ingredients such as opacifiers, emollients, humectants, fragrances, color additives, pH modifiers, and the like. The invention further comprehends methods of administering pharmaceutical agents utilizing the aforedescribed gel bases.

DETAILED DESCRIPTION OF THE INVENTION

The present invention relates to gel bases for pharmaceutical compositions comprising (a) from about 0.5 to about 10.0% by weight $CH_3(CH_2)_{21}(OCH_2CH_2)_nOH$ and from about 90 to about 99.5% of a glycol solvent, or (b) from about 2.5 to about 10.0% by weight $CH_3(CH_2)_x(OCH_2CH_2)_nOH$ and from about 90 to about 97.5% of a glycol solvent, wherein n is an integer from 2 to 30 and x is an integer from 15 to 20, the bases being substantially free of any added gelling agents.

It has been discovered that glycol solvents, specifically propylene glycol and polyethylene glycols having average molecular weights of from about 200 to about 800, can be gelled through the addition of small quantities of the ethoxylated saturated fatty alcohols whose formulas are shown above, i.e., fatty alcohols having chain lengths of from 16 to 22 carbon atoms which are ethoxylated with 2 to 30 moles of ethylene oxide. Indeed, while the ethoxylated alcohols are known primarily as nonionic surfactants, they also form very elegant anhydrous gels with glycol solvents, producing gel bases for pharmaceutical compositions that have excellent drug solubilizing, penetration and release characteristics because of the high percentage of glycol solvent in the gels. In addition, the ethoxylated alcohols act as penetration enhancers for the base.

The term "gel" is used herein in the general sense of a semi-solid, apparently homogeneous substance that may be elastic and jelly-like (as gelatin) or more or less rigid.

The novel gel bases of the present invention can act in themselves as vehicles for active pharmaceutical agents suitable for topical administration in order to achieve a local therapeutic effect, topical administration in order to achieve transdermal or transmucosal penetration and a systemic therapeutic effect, or oral administration. Alternatively, the gel bases can be combined with other ingredients, e.g., diluents, opacifiers, penetrants, coupling agents, fragrances, coloring agents, humectants, moisturizers and the like to provide a total pharmaceutical composition. In addition, for purposes of oral administration, the gels can be incorporated into an oral dosage unit such as a conventional gelatin or other hard capsule, hollow tablet or caplet to provide sustained release from the gel of a pharmaceutical agent upon dissolution of the dosage unit in the gastric juices. Other topical, transdermal, transmucosal and oral dosage forms incorporating the novel gels of the present invention would be readily apparent to those skilled in the medical and pharmaceutical arts.

Preferred concentration ranges (by weight) for the components of the novel gels are from about 0.5 to about 2.5% of ethoxylated behenyl ($C_{22}$) alcohol and from about 97.5 to about 99.5% of a glycol solvent, or from about 2.5 to about 5% of a $C_{16}$–$C_{21}$ ethoxylated alcohol and from about 95 to about 97.5% of a glycol solvent. The preferred range for moles of ethoxylation for all the $C_{16}$–$C_{22}$ alcohols is from 2 to 10. Preferred glycol solvents include propylene glycol and polyethylene glycol having an average molecular weight of about 400.

It has been discovered that within the range of $C_{16}$–$C_{22}$ ethoxylated alcohols, those alcohols with the highest molecular weight prior to ethoxylation (e.g., behenyl alcohol) and the lowest degree of ethoxylation (e.g., 2 to 5 moles) formed gels with glycols readily even in concentrations as low as 0.5–1.0%. Hence, the most preferred ethoxylated alcohol surfactants for use where low concentration of surfactant in the gel base is desired, for example to minimize irritation to the mucous membranes, are behenyl alcohol ethoxylates (2 to 5 moles of ethoxylation). In addition, these preferred surfactants are highly lipophilic and cause better adhesion of the gel to the phospholipid layers of the mucosa in the nasal and oral cavities.

Pharmaceutical agents suitable for incorporation into the gel bases of the present invention or into pharmaceutical compositions incorporating those gel bases include, bu are not limited to, analgesics, decongestants, bronchodilators and other antiasthmatic agents, beta-blockers, antihistamines, anesthetics, antifungals, antinauseants, antiemetics, antibacterial agents, antifungal agents, corticosteroids and anticonvulsants. The concentration of the active ingredient in the gel base is, of course, dependent on the identity of the active agent, the condition and patient being treated and the potency desired.

For purely topical treatment, for example, treatment of a skin area, compositions with excellent release and penetration characteristics can be formed utilizing the gel bases of the present invention and antibacterials, antifungals, local anesthetics, corticosteroids and similar agents, particularly those which are highly soluble in glycol solvents and which are suitable for use with anhydrous vehicles. Compositions intended for systemic administration via the mucosa, e.g., intranasally, buccally or sublingually, can be prepared with the novel gel bases and suitable analgesics, decongestants, bronchodilators, antiasthmatics, antinauseants, anticonvulsants, and other agents where rapid blood level peaks and onset of action are desirable to quickly alleviate the symptoms of the disorder being treated. By virtue of the high glycol solvent content and low surfactant content in the novel gel vehicles, rapid percutaneous and transmucosal absorption are facilitated, and therapeutic blood levels of many agents in these categories can be quickly achieved. Moreover, even at these low concentrations, the selected surfactants augment percutaneous absorption of the active drug ingredient.

Any compatible pharmaceutical agent normally administered orally can be incorporated into the gel bases of the invention and swallowed, with the composition being administered to the patient directly from a tube or packet, or with the gels incorporated as described above into soft or hard capsules, tablets, caplets or other oral dosage forms. Upon dissolution of the hard shell, the novel gel bases provide a smooth, sustained release of active ingredient in the stomach. Alternatively, enteric coatings can be utilized surrounding a gel "core" incorporating the active ingredient to provide sustained release in the intestinal tract.

The gel bases of the present invention may be prepared by any conventional method suitable for combining the ethoxylated alcohol surfactant component with the glycol solvent. By one preferred method, the glycol, for example propylene glycol or a polyethylene glycol having a molecular weight of about 200 to 800, is heated to about 80° C., and the surfactant is then stirred in with the mixture being immediately removed from heat. The mixture is allowed to cool to approximately 60°-65° C., at which point an active pharmaceutical ingredient may be stirred into the gel base until a homogeneous mixture, solution or suspension is achieved.

In the case of certain active drug ingredients which, because of their solubility characteristics, form precipitates or grainy aggregates when added to the gel bases according to the foregoing method, a modified method for combining the active ingredient with the gel is utilized. The gel base is formulated as described above and allowed to cool to about 60°-65° C., at which point the active ingredient is added, but the gel is then reheated to 70°-80° C. until the active ingredient is well-dissolved in the gel. The gel is then allowed to cool slowly to avoid precipitation of the active ingredient. This method was found to overcome solubility problems and enable the formation of elegant gels in the case of most pharmaceutical agents soluble in glycols.

According to another feature of the present invention, it has been discovered that when the gel bases are formulated with ethoxylated behenyl ($C_{22}$) alcohol, they have a remarkable capability for retaining substantial quantities of ethyl or isopropyl alcohol without losing their gel-like consistency. Indeed, gel compositions comprising about 50% by weight of a gel base consisting of ethoxylated behenyl alcohol and propylene or polyethylene glycol, and up to 50% alcohol by weight, have been successfully formulated. These gels with high alcohol content are of great utility in solubilizing active ingredients which are poorly soluble in glycol but highly soluble in alcohol. Moreover, the alcohol contained in the gels exerts a bactericidal and bacteriostatic effect on skin areas to which the gels are applied, and provides a cooling counter-balance to the glycol solvent which may sometimes create a warming sensation when applied to the skin. Gel compositions containing high concentrations of ethyl or isopropyl alcohol may not be suitable, however, for application to the mucosa.

The gel bases disclosed herein provide unique advantages as vehicles or components of vehicles for pharmaceutical compositions. They comprise a nonionic surfactant-containing system which provides for stable solutions of a wide variety of many pharmaceutical agents with little reactivity of surfactant with drug. Moreover, the non-ionic character of the surfactant and the high glycol concentration aids in the penetration of the gel bases with even high molecular weight active ingredients through the skin and mucous membranes.

In addition, the low concentration of surfactant in the gel bases makes them very unlikely to cause irritation, even on the mucosa. Likewise, the high carbon chain length of the ethoxylated alcohol surfactants leads to less likelihood of irritation as compared to short-chained fatty alcohols. Indeed, it has been found that in some instances the ethoxylated alcohol surfactants used in the novel gels act as counter-irritants to relieve irritation that might otherwise be caused by the glycol solvent or the active drug ingredients.

Furthermore, the lack of any need for an extrinsic gelling agent in addition to the surfactant in formulating the novel gel bases renders them inexpensive and simple to formulate, and less likely to cause hypersensitivity reactions than compositions with added gelling agents such as methyl- or ethylcellulose, which leave a residue upon drying and promote microbial contamination.

The viscosities of the subject gel bases range from about 2 to about 4 centipoises. The viscosities of the bases generally increase as the concentration of the ethoxylated alcohol is increased, and bases containing polyethylene glycols have generally higher viscosities than those with propylene glycol. When active pharmaceutical agents are incorporated into the gel bases to form gel-like pharmaceutical compositions, the viscosities of said compositions range from about 2.5 to about 7.5 centipoises, with the polyethylene glycol-containing compositions generally exhibiting higher viscosities.

Gel pharmaceutical compositions including the novel gel bases of the present invention and active pharmaceutical agents may be administered by a variety of methods, depending on the activity of the pharmaceutical agent or agents incorporated in the gel and the condition being treated. Such methods of administration include squeezing the drug-containing gel directly from a tube or other container onto an affected tissue area and spreading a thin film of the gel over that tissue area for topical treatment; inserting the tip of a tube or other suitable container into the nostrils and administering an effective dosage amount of the gel into the nasal passages for rapid dissolution and transmucosal absorption; similar direct application of the gel for transmucosal absorption on other mucous membrane areas, including buccal and sublingual administration; and oral administration of an effective dosage amount of the gel composition directly or within a soluble, orally ingestible outer shell, such as in capsules, tablets or caplets, as described previously. Other suitable uses and routes of administration for the subject gel bases and pharmaceutical compositions including the same will be apparent to those skilled in the medical and pharmaceutical arts.

Among the therapeutic advantages provided by the novel gel bases and gel compositions containing the same are more rapid and more complete percutaneous absorption of topically active pharmaceutical agents, such as corticosteroids, in comparison with conventional topically applied bases. It is believed that various advantageous features of the novel gel bases, including their high glycol content, their nonionic and anhydrous character, and the absence of any added or extrinsic gelling agents, promote more rapid absorption of topical agents through the outer skin layers and the mucosa.

It has also been discovered that certain drugs conventionally utilized for systemic therapy only in the form of salts or esters, not free bases, can be effectively administered transmucosally in free form when incorporated into the novel gel bases. Examples of such drugs include albuterol (normally administered as the sulfate) and propranolol (normally administered as the hydrochloride).

The following examples provide detailed illustrations of the compositions and methods of the present invention. These examples are not intended, however, to limit or restrict the scope of the invention in any way, and should not be construed as providing methods, conditions, ingredients or starting materials which must be utilized exclusively to practice the present invention.

EXAMPLES 1-10

Gel Bases with Ethoxylated Behenyl Alcohol 10 grams each of ten gel bases were prepared using the ethoxylated behenyl alcohol surfactants and glycol solvents indicated in the following table, in the respective weight percentages given. In each instance, the glycol solvent was initially heated to about 80° C. in a beaker and the surfactant was then rapidly stirred into the glycol, with the mixture being immediately removed from heat and allowed to cool to ambient temperature.

| Percentages of Ingredients (w/w) | |
|---|---|
| Ex. 1 | Ex. 2 |
| 0.5% beheneth-2* | 1.0% beheneth-2 |
| 99.5% propylene glycol U.S.P. | 99.0% propylene glycol U.S.P. |
| Ex. 3 | Ex. 4 |
| 1.0% beheneth-5 | 2.5% beheneth-5 |
| 99.0% propylene glycol U.S.P. | 97.5% PEG 400** |
| Ex. 5 | Ex. 6 |
| 2.5% beheneth-5 | 5% beheneth-20 |
| 97.5% propylene glycol U.S.P | 95% PEG 400 |
| Ex. 7 | Ex. 8 |
| 5% beheneth-30 | 10% beheneth-5 |
| 95% PEG 400 | 90% propylene glycol U.S.P. |
| Ex. 9 | Ex. 10 |
| 10% beheneth-20 | 10% beheneth-30 |
| 90% PEG 400 | 90% propylene glycol U.S.P. |

*CFTA nomenclature for behenyl alcohol, 2 moles of ethoxylation. Other "beheneth" designations are likewise followed by number of moles of ethoxylation.
**Polyethylene glycol having average molecular weight of about 400 - Dow Chemical Company.

EXAMPLES 11-18

Gel Bases with Ethoxylated Cetyl and Stearyl Alcohols 10 grams each of the following eight gel bases were prepared in accordance with the method described in connection with Examples 1-10:

| Percentages of Ingredients (w/w) | |
|---|---|
| Ex. 11 | Ex. 12 |
| 2.5% ceteth-2* | 2.5% ceteth-20 |
| 97.5% propylene glycol U.S.P. | 97.5% PEG 400 |
| Ex. 13 | Ex. 14 |
| 5% ceteareth-5** | 5% steareth-5*** |
| 95% propylene glycol | 95% propylene glycol |
| Ex. 15 | Ex. 16 |
| 5% ceteth-5 | 5% ceteareth-30 |
| 95% PEG 400 | 95% propylene glycol |
| Ex. 17 | Ex. 18 |
| 10% ceteth-2 | 10% steareth-10 |
| 90% PEG 400 | 90% propylene glycol |

*CFTA nomenclature for ethoxylated cetyl alcohols.
**CFTA nomenclature for ethoxylated cetyl/stearyl alcohol mixtures.
***CFTA nomenclature for ethoxylated stearyl alcohols.

EXAMPLE 19

Pharmaceutical Compositions 50 gram batches of gel bases were prepared according to Examples 4 (97.5% PEG 400, 2.5% behenth-5) and 5 (97.5% propylene glycol, 2.5% beheneth-5). As each batch cooled to 60°-65° C., one of the active pharmaceutical agents indicated in Table 1 (below, following Example 20) was added in the amount indicated. In some instances, the active ingredient readily dissolved or was well suspended in the gel base; in other instances, the gel had to be reheated to 70°-80° C. after addition of the active ingredient and then slowly cooled to form a homogeneous, drug-containing gel. Table 1 indicates whether the first, standard ("STAND.") procedure was used or whether the second, modified ("MOD.") procedure was used in each instance. The Table also indicates whether the gel base contained PEG 400 ("PEG") or propylene glycol ("PPG").

EXAMPLE 20

Drug Release Study

An in vitro dissolution study was conducted with, among others, the gel compositions prepared according to Example 19 to determine whether the gels actually release a substantial proportion of the active ingredient into an aqueous medium over a short period of time, which is a prerequisite for utility as an orally administered medication.

Dissolution was carried out on the Van Kel 6 Spindle Dissolution Apparatus. This apparatus is composed of a waterbath, six cylindrical vessels, six spindles with paddles attached, and the controlling unit. The parameters for dissolution U.S.P paddle method were kept constant: waterbath temperature: 37° C.; rotating speed: 50 RPM; volume of distilled water in vessels remained 500 or 400 mls. When 5 ml samples were drawn out, 5 ml of fresh gel was replaced in order to keep sink conditions. Six 5 ml samples were taken at 2, 5, 10, 20, 30 and 40 minutes for each run. Once the samples were completed and the standards were prepared, assay by UV spectrophotometer was performed, using the Hewlett Packard single beam microcomputer controlled general purpose spectrophotometer.

The standards were assayed first at the wavelength proposed by literature (all of which were identical). With the microcomputer attached to the UV, the status concentration program established linearity in the standard curve generated by the standards giving the % error or deviation from that curve. From that point on, when the samples were assayed, concentration values were produced directly. The average concentration of each drug released after 40 minutes is given below on Table 1.

TABLE 1

| Drug (PPG or PEG base) | Dose (mg) | Gel Procedure | Average % release |
|---|---|---|---|
| Nitroglycerin (PPG) | 10 | STAND. | 50 |
| Phenylpropanolamine HCL (PPG) | 50 | STAND. | 37 |
| Phenylpropanolamine HCL (PEG) | 100 | STAND. | 66 |
| Albuterol base (PPG) | 10 | STAND. | 32 |
| Propranolol HCL | 10 | MOD. | 28 |
| Metaproterenol SO4 | 10 | MOD. | 27 |
| Ibuprofen (PPG) | 200 | STAND. | 25 |
| Ibuprofen (PEG) | 400 | STAND. | 32 |
| Meclizine (PPG) | 12.5 | STAND. | 23 |
| Diphenhydramine (PPG) | 25 | STAND. | 21 |
| Theophylline (PPG) | 200 | MOD. | 18 |
| Albuterol SO4 (PPG) | 10 | MOD. | 17 |

EXAMPLE 21

Vasoconstriction Study

The in vivo drug release characteristics of the gel bases on topical application were studied by comparing the relative vasoconstrictive activity of two corticosteroid-containing gel compositions according to the present invention with commercial cream and ointment formulations of the same active ingredient.

The two gel bases contained respectively 1% beheneth-2 and 99% propylene glycol (Gel A) and 2.5% beheneth-2 and 97.5% propylene glycol (Gel B). The commercial products were KENALOG Cream-0.1% and KENALOG Ointment-0.1% (E. R. Squibb & Sons, Inc.). All of the test products contained 0.1% triamcinolone acetonide, a topically active corticosteroid. Sixteen healthy, adult volunteers participated as subjects in this study.

After washing the forearms with a bland soap and patting dry with a soft towel, two circular sites, each measuring 1.2 centimeters in diameter were outlined with ink on the volar aspect of the forearm of each subject. Ten microliters (ul) of each of the test products was then delivered to a designated test site. Test product application randomized. The test products were spread uniformly within the test area using thin glass rods. The test sites were then protected from rubbing against clothing, etc. by covering them with perforated plastic weighing cups which were taped at the edges to the skin.

After four (4) hours the cups were removed and the entire forearm was washed again with soap and water and blotted dry with a towel.

The degree of blanching at each test site was graded 30 minutes, after the products had been washed from the skin and again at 6 hours and at 24 hours after application of the test products. Grading of responses was performed under standardized lighting by the same evaluator (the investigator), who did not participate in the application of the test materials and who was unaware of the product assignment to the test sites. The following clinical grading scale was used:

0=No vasoconstriction
1=Minimal visible blanching with ill-defined borders
2=Definite blanching with well-defined borders
3=More intense blanching
4=Intense blanching, spreading beyond the application site No adverse experiences were recorded following the application of any of the test products. Statistical analysis using Friedman's ANOVA and the individual total scores at 4, 6 and 24 hours revealed that the four treatments were significantly different (P=0.0300). The cumulative vasoconstriction scores for the 16 subjects were as follows:

KENALOG Ointment (0.1%)=6
KENALOG Cream (0.1%)=21
Gel A=31
Gel B=33

Under the presently described test conditions, both gel formulations A and B exhibited a similar vasoconstrictor profile and both were superior to the KENALOG 0.1% formulations.

It has thus been shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A pharmaceutical composition comprising a gel base including:
   (a) from about 0.5 to about 10.0% by weight $CH_3(CH_2)_{21}(OCH_2CH_2)_nOH$ and from about 90 to about 99.5% of a glycol solvent, or
   (b) from about 2.5 to about 10.0% by weight $CH_3(CH_2)_x(OCH_2CH_2)_nOH$ and from about 90 to about 97.5% of a glycol solvent, wherein n is an integer from 2 to 30 and x is an integer from 15 to 20, the base being anhydrous and substantially free of any added gelling agents, and a topically, systemically or orally active pharmaceutical agent dissolved therein or admixed therewith.

2. A composition according to claim 1, wherein said pharmaceutical agent is selected from the group consisting of analgesics, decongestants, bronchodilators, antiasthmatics, beta-blockers, antihistamines, anesthetics, antifungals, antinauseants, antiemetics, antibacterial agents, antifungal, corticosteroids, anticonvulsants.

3. A composition according to claim 1, wherein said pharmaceutical agent is selected from the group consisting of nitroglycerin, phenylpropanolamine hydrochloride, albuterol, albuterol sulfate, propranolol hydrochloride, metaproterenol sulfate, ibuprofen, meclizine, dyphenhydramine and theophylline.

4. A composition according to claim 1, wherein said pharmaceutical agent is a free base.

5. A method of administering a topically active pharmaceutical agent to an affected tissue area of a patient comprising the incorporation of said pharmaceutical agent into a gel composition according to claim 1 and the subsequent application of a thin film of said gel composition to the affected area.

6. A method of administering a systemically active pharmaceutical agent to a patient requiring treatment with said agent which comprises the incorporation of said agent into a gel composition according to claim 1 and the subsequent application of said composition to the mucous membranes of the patient.

7. A method according to claim 6 wherein an effective dosage amount of said gel composition is administered to the patient intranasally, buccally or sublingually.

8. A method of administering an orally active pharmaceutical agent to a patient requiring treatment with said agent which comprises the incorporation of said agent into a gel composition according to claim 1 and the subsequent oral administration of said gel composition to the patient.

9. A method according to claim 8 wherein an effective dosage amount of said gel pharmaceutical composition is swallowed directly by the patient.

10. A method according to claim 8 wherein the patient is orally administered a capsule, hollow tablet or caplet which contains an effective dosage amount of said gel composition.

* * * * *